United States Patent [19]

Glenn

[11] Patent Number: 4,857,063

[45] Date of Patent: Aug. 15, 1989

[54] SURGICAL ASPIRATOR

[75] Inventor: Luke H. Glenn, Ogden, Utah

[73] Assignee: USA Medical, Ogden, Utah

[21] Appl. No.: 145,262

[22] Filed: Jan. 19, 1988

[51] Int. Cl.$^4$ .............................................. A61M 1/00
[52] U.S. Cl. .................................................... 604/317
[58] Field of Search ...................................... 128/303.1;
  604/317–319, 902, 905, 22, 30; 285/276, 277;
  224/42, 45 R, 148

[56] References Cited

U.S. PATENT DOCUMENTS

| | | | |
|---|---|---|---|
| 2,678,159 | 5/1954 | Ellis | 604/317 |
| 2,784,717 | 3/1957 | Thompson | 604/319 |
| 3,785,380 | 1/1974 | Brumfield | 604/902 |
| 4,258,717 | 3/1981 | Bisera et al. | 604/30 |
| 4,617,013 | 10/1986 | Betz | 604/35 |
| 4,647,081 | 3/1987 | Landgraf et al. | 285/276 |
| 4,688,569 | 8/1987 | Rabinowitz | 128/303.14 |

OTHER PUBLICATIONS

Site XTR Catalog Cut, Site Microsurgical Systems Inc., Horsham, Pa. 19044, 1984.

Gast Catalog, Gast Manufacturing Corp., Benton Harbor, Mich. 49022, Nov. 1978.

*Primary Examiner*—Jerome L. Kruter
*Attorney, Agent, or Firm*—M. Reid Russell

[57] ABSTRACT

A portable surgical aspirator (10) for use in removing body fat and fluids by drawing same under vacuum through a cannula (52) that is inserted beneath a person's skin performing a liposuction surgical procedure. The aspirator is maintained in a single housing (11) that is caster mounted for ease of movement and includes dual oilless vacuum pumps (15) mounted to opposite ends of an electric motor (14) that can be operated from a manual switch (27) located on the housing or a remote foot switch (65). Pump (15) operation provides, through a single vacuum (18) port, nearly one atmosphere of vacuum within three seconds. The vacuum port (18) is connected through hoses to vacuum bottles (34) and (38) that are for collecting fat and body fluids, passed through tubing from the cannula. The vacuum bottles are maintained in a bottle caddy (56) that is arranged for releasable attachment to the aspirator housing. The aspirator includes a handle (22) that, with the handle ends (23a) and (23b) secured to the aspirator housing is centrally gripped by an operator for carrying the device, or, with one handle end released, and the handle (22) pivoted around its other end, the released handle end can receive an operator's hand for manually pulling the device rolling on its casters.

18 Claims, 3 Drawing Sheets

SURGICAL ASPIRATOR

BACKGROUND OF THE INVENTION

1. Field of the Invention

This invention relates to surgical aspirators for use in a surgical procedure performed by a medical doctor to remove fat from beneath a patient's skin.

2. Prior Art

Currently, a number of aspirator devices have been developed for use in surgical procedures for removing fatty tissue from beneath a patient's skin. Such devices, like the present invention, have been exclusively manufactured and sold to medical practitioners who, within the confines of the hospital or their office, perform this procedure on patients. Such procedure requires insertion of a cannula or a wand-type suction device beneath the patient's skin and pulling the fatty material therethrough with a vacuum. In such procedure the fatty tissue and liquids are passed through the cannula and connected line or hoses and are deposited in a vessel for disposal. Such aspirator, to be effective, needs to have a capability of generating a strong vacuum to one (1) atmosphere. Also, of course, as the device is used in a medical procedure, the components that are for insertion into or may come in contact with the patient's body must be capable of being sterilized or replaced after use.

While such aspirator devices as set out above are not new, prior to the present invention they have been generally large, bulky and unwieldy and are not truly portable as is the present invention. Typical of such earlier aspirators, several aspirator devices are presently offered by Dean Medical Instruments, Inc., that are identified as models 500 and 500-2. These units, similar to the present invention, provide a capability for varying a produced vacuum to nearly one (1) atmosphere and use multiple vessels for receiving and collecting the fatty materials from the patient, and even involve assorted sizes and configurations of suction wands or cannula for use with the device. The Dean Medical line of aspirators, however, does not provide a unit that is easily portable, nor does it involve a versatile handle structure that can be used to drag or carry the device. Also, none of the Dean Medical devices provide a bottle or vessel arrangement and caddy or carrier therefore that is like the arrangement taught by the present invention.

Similar to the Dean Medical line of aspirators, an aspirator manufactured by Berkeley Medivices, Inc. known as a SYNEVAC TM GP SYSTEM 5 will provide nearly one (1) atmosphere of vacuum and is a caster-mounted unit. This SYNEVAC TM GR SYSTEM 5 is not intended to be portable and does not involve a structure like that of the present invention. Nor does it employ two (2) identical bottles or vessels. The vessels it utilizes are maintained in individual mounts on the unit rather than in a bottle tray or caddy that can easily be installed to and removed from nesting engagement on a housing of the invention.

Additionally, an aspirator device manufactured by Wells Johnson Company, identified as Aspirator II, like the above-cited aspirators are caster mounted and include two (2) suction vessels for collecting fatty tissue and liquids that are shown as different size bottles. This Wells Aspirator II is like the earlier cited aspirators in that it is not intended to be portable as is the present invention. Nor does it involve a bottle or vessel carrier or caddy like that of the present invention.

Another earlier aspirator device that has been sold in France is manufactured by Laboratoires Sebbin of Suresnes, France and is identified as Lipo-Sebbin. This device, like the present invention, also employs two (2) vessels of equal size, can be operated from a remote foot pedal and is caster mounted. This device, like the above discussed aspirators, however, does not employ a removable vessel or bottle carrier or caddy nor does it include a handle structure like that of the present invention for alternatively carrying or dragging the device.

SUMMARY OF THE INVENTION

It is, therefore, a general object of the present invention to provide a caster mounted portable surgical aspirator for use in performing a liposuction procedure where unwanted body fatty tissue is aspirated from beneath a patient's skin.

Another object of the present invention is to provide an aspirator for use in a liposuction procedure that is capable of producing a nearly one (1) atmosphere of vacuum, pulling a suitable volume of air so as to efficiently remove fatty tissue, which tissue is passed to collection vessels or bottles that are arranged to be easily removed and replaced during the procedure as each is individually filled.

Still another object of the present invention is to provide a cannula or suction wand as part of the surgical aspirator that includes a quick disconnect coupling whereby the cannula can be quickly and easily detached from or installed to a suction line end coupling during a surgical procedure, which individual cannula are constructed to be suitable for sterilization in a conventional autoclave unit.

Still another object of the present invention is to provide, in line with the suction line and the cannula or suction wand, a one-way control valve for prohibiting a back-flow of materials as could travel into a patient's body.

Still another object of the present invention is to provide an aspirator device that is compact and light in weight that includes a handle arrangement that can be configured to drag or lift the device to be easily and conveniently moved within the setting of either an operating room or a doctor's office.

Still another object of the present invention is to provide, as a component of the aspirator, a vessel or bottle caddy that is releasably installed to nest to the aspirator housing and is to maintain two (2) identical vessels or bottles that each receive and accommodate stoppers fitted thereover, whereto vacuum hoses are connected, the one bottle to serve as a vacuum reservoir with the other for collecting fatty tissue therein, which bottles can then be individually removed and replaced with minimum interruption to the surgical procedure.

Still another object of the present invention is to provide an aspirator device that is simple to use, is light in weight and is easily moveable and includes components that come in contact with a patient arranged to be easily removable for sterilization in a conventional autoclave unit.

In accordance with the above objects, the present invention is in a portable surgical aspirator that incorporates a housing that is preferably rectangular in shape and is formed from a high impact plastic for mounting to a supporting base plate. The base plate incorporates casters at each corner thereof allowing the plate and housing thereon to be rolled along a floor. The aspirator components and their arrangement to the base plate is such as to provide a minimum weight that is well distributed between the base plate ends.

Within the housing, secured to the base plate, is a suction arrangement that is preferably a single electric motor that drives dual rotary vane oilless pumps, the pumps to provide a rapid vacuum response to pull nearly a full atmosphere of vacuum in less than three (3) seconds, evacuating up to two (2) liters of air in less than ten (10) seconds. This suction arrangement will produce a high flow rate of one hundred fourteen (114) liters of air per minute. The aspirator includes a flow control valve that is connected appropriately to the suction arrangement to control the amount of vacuum between zero (0) to a maximum vacuum of nearly one (1) atmosphere. A fan is included within the housing to keep the vacuum pumps cool. On a housing top surface is installed a pressure gauge that is connected to preferably display available vacuum in both negative inches of mercury and negative atmospheres. Additionally, two (2) manual switches are provided on the housing top surface for controlling, respectively, the operation of the fan motor and electric motor driven suction pumps. A vacuum inlet port extends as a tube from the housing top whereover an in-line filter is telescoped for collecting any liquids or fatty matter as may have inadvertently passed through a vacuum line from a collection vessel.

The vacuum pumps, through the filter, provide a vacuum source that connects through an open hose into a first vessel or bottle. The first bottle is connected serially through an open connecting line to a second vessel or bottle that is, in turn, connected through an appropriate suction line or hose and one-way control valve to a suction wand or cannula. A number of suction wands or cannula can be used interchangeably, with each formed to have a contoured handle to accommodate an operator's hand and is constructed from a bakelite plastic-type material suitable for sterilization in an autoclave unit. A wand or open tube extends from the handle that is formed from a metal, such as a stainless steel to be suitable for autoclave sterilization. The suction wand or cannula handle includes a coupling end opposite to the open tube end for releasably fitting into a socket. The socket, when the cannula handle end is inserted therein, provides a gate lock that allows full rotation of the cannula handle within the socket and is released by depression of a trigger portion thereof. With the cannula so installed, it is free to rotate through three hundred and sixty (360) degrees about its coupling to that vacuum hose, the cannula tube end for fitting through an incision to beneath the patient's skin.

The aspirator housing and components are selected and assembled to be light in weight, the unit weighing approximately fifty (50) pounds, and is therefore liftable by one person. To accommodate either lifting or pulling the aspirator from place to place, a unique handle structure is provided. The preferred handle includes one end that is pivotally coupled at one edge of the housing top. The handle spans the housing with the other handle end arranged for releasable attachment to the opposite housing top edge. The housing top further includes a center cavity for passing or allowing an operator's hand to fit therein to curl around a center portion of the handle. The handle attachment end, when uncoupled, includes a cross piece for use as a gripping surface allowing an operator to drag or pull the device, the unit rolling on its casters.

As set out above, the invention includes a dual vessel or bottle system with a vacuum created in the bottles, the one bottle to serve as a reservoir with the fatty tissue pulled into the second bottle. The bottles are connected serially through hoses. So arranged, as one bottle fills, the other bottle can be moved over to replace it and an empty bottle moved into position, which bottle change over will minimally disrupt the surgical procedure. The bottles are arranged in a bottle carrier or caddy that is designed for releasable mounting in nesting arrangement to the aspirator housing top. The bottle caddy is maintained to that housing top by a catch that is integral to that housing top and will fit over a center upstanding side wall area of the bottle caddy nested in an appropriate contoured section of that housing top to hold that bottle caddy in place. In practice, when it is determined to move the bottles, the caddy with the bottles therein an be moved as a unit.

DETAILED DESCRIPTION OF THE DRAWINGS

Figure 1:
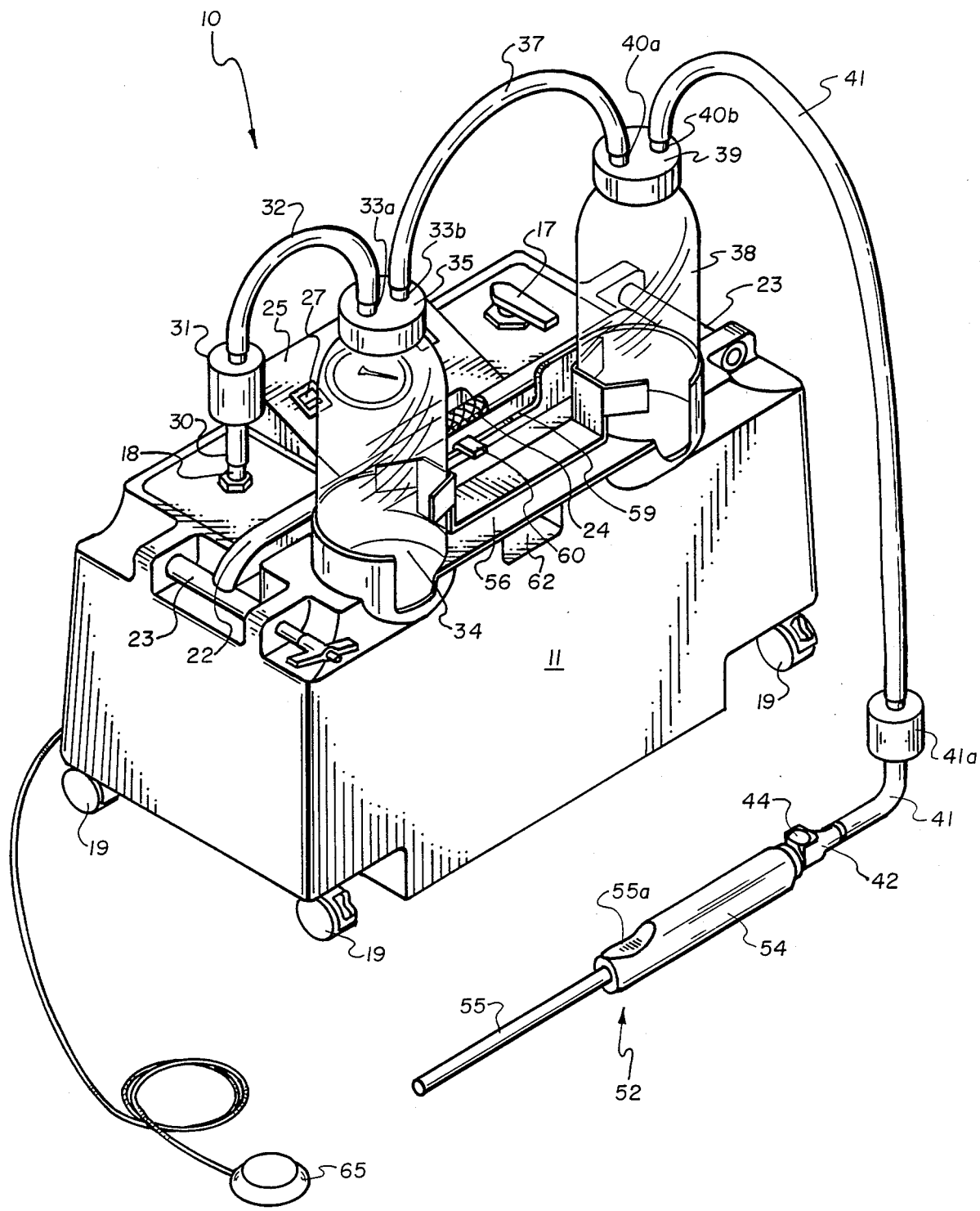
FIG. 1 is a side elevation perspective view showing the portable aspirator of the present invention.
Figure 2:
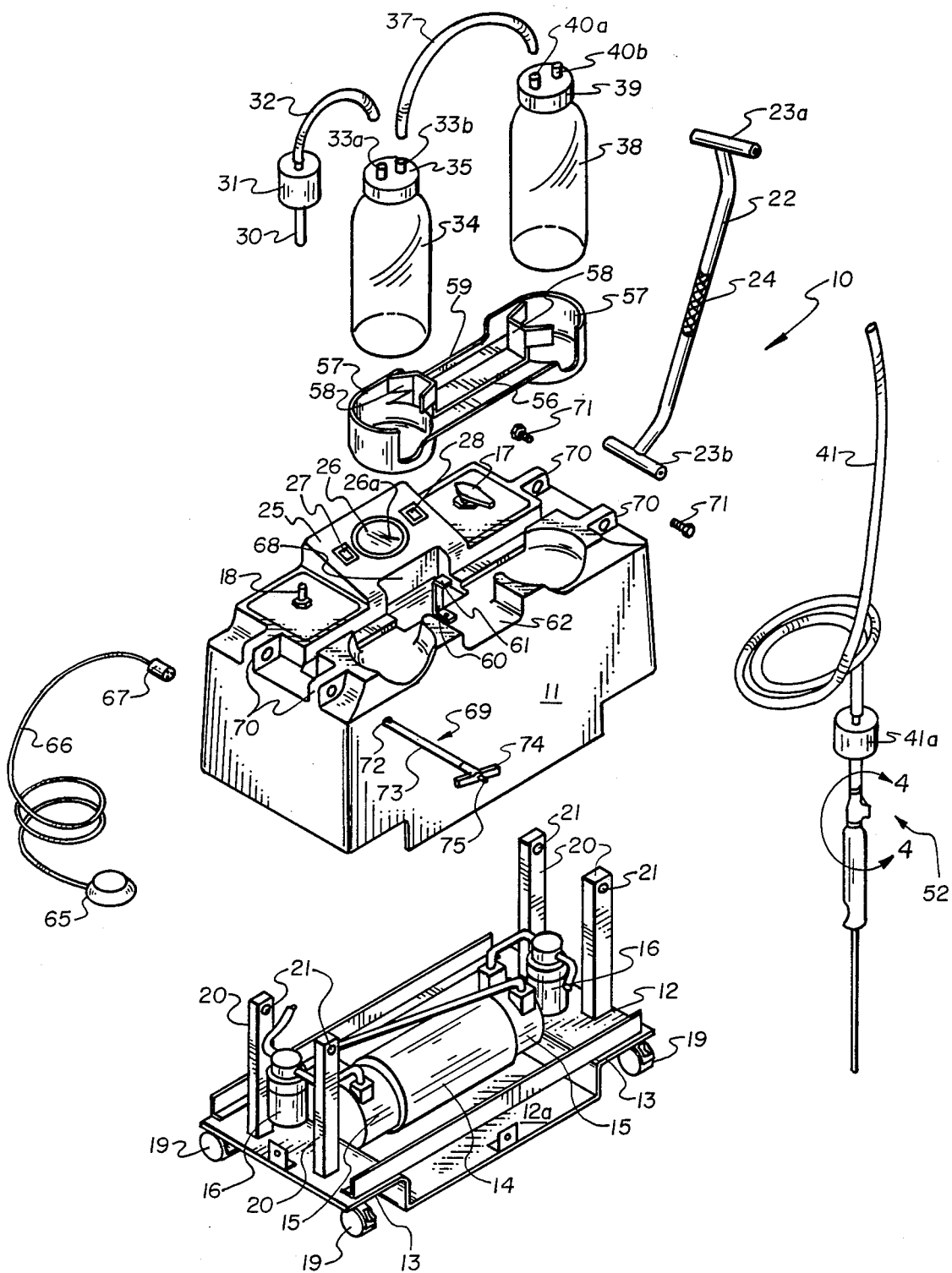
FIG. 2 is a view of the portable aspirator of FIG. 1 showing components thereof exploded apart.

FIG. 1 shows a profile perspective view of the present invention in a portable surgical aspirator 10, hereinafter referred to as "aspirator" that is for use in a surgical procedure for removing unwanted fatty tissue and fluid from beneath a patient's skin. FIG. 2 shows the aspirator 10 of FIG. 1 exploded apart, showing a housing 11 exploded off of a base plate 12. Base plate 12 is formed to be underslung, the opposite ends bent upwardly at a first right angle and outwardly at a second right angle to provide flat surfaces 13 whereto at the corners, casters 19 are attached. A center flat portion 12a of plate 12 is thereby set below flat surfaces 13 for supporting a motor 14 that mounts on its opposite ends rotary vein oilless pumps 15. The dual pumps 15, in turn are connected through pressure transfer lines to regulators 16, respectively. The pumps 15 when turned by motor 14, provide a vacuum that, on demand, will approach an atmosphere of pressure, on twenty-nine (29) plus inches of mercury (Hg), the regulator 16 routing the vacuum through a flow control valve 17. Flow control valve 17 is shown as a handle that extends outwardly from a flat surface that is formed in a right side of a molded top portion of housing 11. In practice, the vacuum capacity is controlled between zero inches of mercury (Hg) to a minus twenty-nine (29) plus inches of mercury (Hg) by appropriately positioning the handle 17, which handle is turned clockwise.

Shown best in FIGS. 1 and 2, the generated vacuum is present at a vacuum port 18, which port is shown as an open tube that extends outwardly from a second flat portion formed in the left side of the housing top, the vacuum port 18 on line with, and spaced apart from, the vacuum control valve 17. Vacuum port 18 is to receive an end of a filter hose 30 telescoped thereon.

Figure 3:
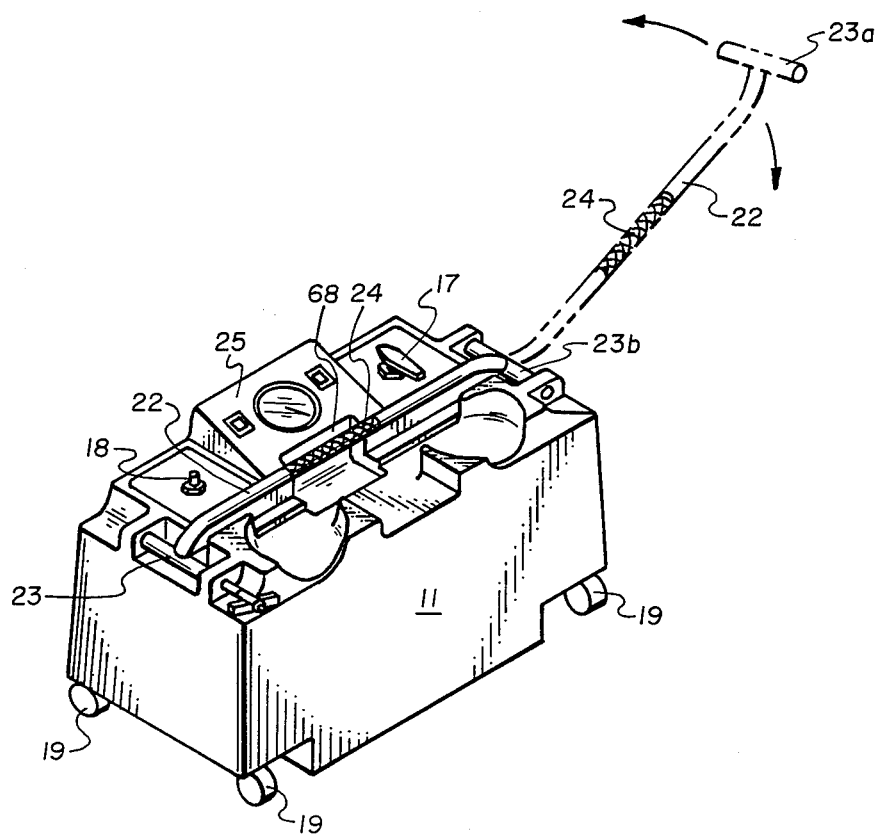
FIG. 3 is a view like FIGS. 1 and 2, only showing a handle assembly thereof rotated to a dragging attitude.

Portability is provided to the aspirator 10 by casters 19 that are mounted at the corners of upwardly stepped base plate ends 13, two or more of which casters 19 may be locking type casters whereby an operator, with their toe, can lock the caster wheels in place. Shown in FIG. 2, in addition to the components described hereinabove, the base plate further includes pairs of upright standards 20. The individual standards of each pair are parallel and are spaced apart from one another at right or normal angles from top surfaces of the base plate ends 13. The standards 20 are holed appropriately near their top ends at 21. Holes 21 of each pair are to align to receive bolt type fasteners fitted therethrough. The holes 21 of one pair of standards to receive bolt fasteners 71 that fit into and provide a pivot coupling to cross piece end 23b of a handle 22. Handle 22 functioning will be described in detail hereinbelow. The handle, shown in FIG. 3, is arranged to span across housing 11 between its pivot coupling at cross piece 23b to a releasable coupling at its opposite cross piece end 23a. The handle 22 middle portion 24 is preferably knurled or otherwise prepared to receive a person's hand fitted therearound.

The housing 11, as shown best in FIGS. 1 and 2, is preferably contoured with a recess at 68 below the handle middle portion 24 to accommodate a person's hand fitted therearound. The housing, shown best in FIGS. 2 and 3, includes a center forwardly tilted control panel 25, located between the vacuum control 17 and vacuum port 18 wherein are mounted a vacuum gauge 26, with indicator needle 26a, and switches 27 and 28. To provide the above-described housing top portion panels and recesses, the housing 11 is preferably manufactured from a plastic material as by casting or vacuum forming methods from a material to have impact resistance. Also formed in that housing top portion are shown spaced circular recesses with a rectangular recess 62 therebetween adjacent to the handle recess 68. These recesses serve to receive and contain, nested therein, a bottle tray or caddy 56 for maintaining vessel or bottle 34 and 38, as will be set out hereinbelow.

The housing 11 is formed to have a rectangular shape tapering from a greater area at an open bottom portion, whereto the base plate 12 is secured, to a lesser cross-sectional area at the top portion, which top portion is configured to accommodate the described recesses, vacuum control 17 and vacuum port 18, with the forward sloping panel portion 25 centered therebetween. Switch 27, arranged on the left side of that center panel 25, as shown in FIG. 2, is preferably to connect the motor 14 to a source of electricity, the motor operating to turn the dual rotary vane oilless pumps 15, hereinafter referred to as "pumps". When switch 27 is depressed, the motor 14 is operated such that, within a short time span of approximately three (3) seconds the pumps will provide a vacuum to nearly one (1) atmosphere, available through valve 17 to vacuum port 18. The available vacuum at port 18, is shown at gauge 26, by the positioning of a pointer 26a on a scale. In practice, a preferred motor with dual rotary vane oilless pumps connected to opposite ends thereof is manufactured by ITT Pneumotive, Inc. of Monroe, La., identified as TA-0040-2V-991050. This arrangement includes a one-third ($\frac{1}{3}$) horse power motor and has been used in practice to provide the nearly one (1) atmosphere of vacuum in approximately three (3) seconds. It should, however, be understood that a greater or lesser power of electric motor could be employed for the aspirator 10 within the scope of this disclosure. The preferred rotary vein oilless pumps have a capability for evacuating approximately three (3) liters of air in less than ten (10) seconds, with a volume capability of four (4) cubic feet per minute.

Shown in FIG. 2, the switch 28 is for operating a fan, not shown, that is arranged within the housing 11 for controlling temperature. Depending upon the use of the device, the fan may be considered to be optional.

As set out above, with the switches 27 and 28 turned on, a vacuum will be available at the vacuum port 18. This vacuum port, as shown best in FIGS. 1 and 2, receives an end of filter hose 30, the opposite end of which hose is connected to one side of a filter 31. Filter 31 is provided for restricting back flow of fluid materials collected during operation that could contaminate pumps 15. A filter manufactured by Gelman Sciences, Inc. of Ann Arbor, Mich., identified as Bacterial Filter 20-5200 has been used in practice for this purpose. To the output end of filter 31 is connected a vacuum hose 32. The opposite end of which vacuum hose 32 fitted into a stopper connector 33a that is, in turn, fitted through a stopper 35. The stopper 35 is installed over in sealing engagement an open neck end of a first collection vessel or bottle 34. The stopper 35 is preferably a rubber or like flexible stopper. Operation of the vacuum pumps 15 will therefore create, through vacuum hose and stopper connector 33a, a vacuum within bottle 34. Stopper 35 includes a second connector 33b that also opens to within bottle 34 and is linked by a connector hose 37 to a first connector 40a of a second stopper 39. The second stopper 39 is also for fitting over to seal or close off an open neck end of a second vessel or bottle 38. Vessels or bottles 34 and 38 are preferably identical as are stoppers 35 and 39, and each stopper includes, respectively, two (2) each first and second connectors 33a and 33b and 40a and 40b fitted therethrough. First connector 40a is for linking the vessels together through connector hose 37 and second connector 40b to receive fitted thereover one end of a cannula hose 41.

Operation of the vacuum pumps 15 therefore provides a vacuum that is present in both bottles 34 and 38 and at the cannula hose 41. In practice, air will be quickly evacuated from the respective bottles 34 and 36, the created vacuum quickly equaled therebetween and at an open end of a cannula tube 55 of cannula 52. This vacuum pulls materials collected through the cannula tube 55 end that are passed into and are collected in bottle 38. In operation, it is preferred that the bottles either be switched or that a new bottle 38 changed for the old bottle 38 as that old bottle is filled such that there will be one bottle 34 that remains essentially empty during this procedure.

Figure 4:
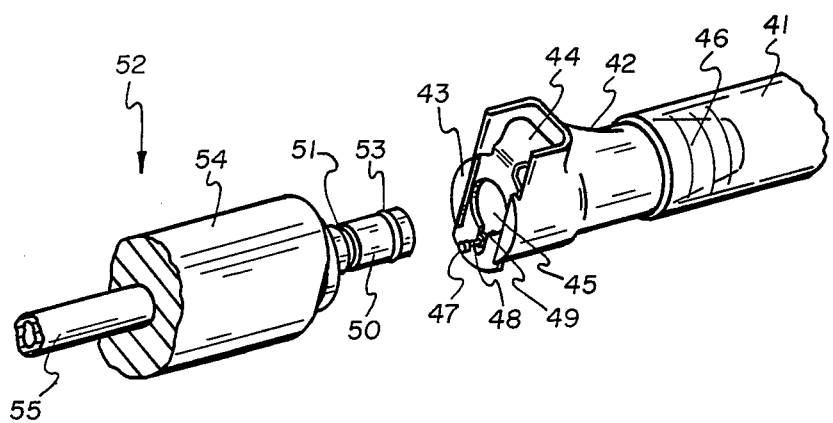
FIG. 4 is an expanded sectional view taken within the line 4—4 of FIG. 2 showing a cannula handle coupling end portion exploded away from a suction line coupling.

The cannula hose 41 connects on its end opposite to its coupling to second connector 40b to a cannula coupling 42, as shown best in FIG. 4. The cannula coupling 42 includes a gate 43 and trigger portion 44 that extends from one end thereof. The trigger portion 44 is folded approximately ninety (90) degrees to the gate 43 and when manually depressed causes the gate 43 to travel against a spring biasing, not shown. A passage 45 through gate 32 is thereby brought into alignment with a longitudinal opening in cannula coupling 42. This longitudinal opening extends through the cannula coupling 42 and ridged connector end 46 whereover the cannula tube 41 is telescoped. Moving gate 43 to where its passage 45 will align with the coupling 42 longitudinal opening also causes a pin 47, that extends outwardly from the connector end, to travel into a slot 48 that is formed in that gate opposite to trigger portion 44 and intersecting passage 45. The pin 47 is also spring biased outwardly from the connector end and includes a groove therearound to receive a side of gate slot 48 so as to lock thereto until the pin 47 is depressed when the cannula 52 is fitted thereto. On depressing of the pin 47 by contact of the pin 47 end by a cannula handle portion 54, the lesser diameter portion of the pin 47 will travel inwardly to align with the apex end of the gate slot 48, thereby allowing that gate to move upwardly under the urging of a spring, not shown. Thereby, the passage 45 through gate 43 will move out of alignment with the longitudinal opening through the cannula coupling 42. In this unaligned state, an arcuate edge section 49 of the passage 45 that is adjacent to the slot 48 will travel across the cannula coupling longitudinal opening. This arcuate section 49 has a thickness to fit into a circumferential slot 51 that is formed around a coupling end 50 of cannula 52. So arranged, when the gate 43 is moved responsive to its spring biasing, the gate arcuate section 49 will enter into the circumferential slot 51 of cannula 50, locking that cannula to the cannula coupling. In this locking, as the slot 51 is circumferential and uniform, the cannula is allowed to rotate through a full circle of three hundred sixty (360) degrees. A sealing of that cannula coupling end 50 within the cannula coupling 42 is provided by a sealing ring or O-ring 53 that is fitted into a circumferential groove formed around cannula coupling end 50, forward of the slot 51.

Shown in FIGS. 1 and 4, the canula 52, in addition to its coupling end 50, includes a handle portion 54 that is shown in the cross-section in FIG. 4 as preferably manufactured from a plastic material. An open cannula tube 55 is implanted to extend through handle portion 54. The open cannula tube 55 is the component of the aspirator 10 that is for fitting under a patient's skin to pull fatty tissue and liquid through an open end thereof, that material ultimately passing into bottle 38. Dependent on the specific procedure, the open cannula tube 55 can be manufactured in a number of configurations and lengths as appropriate for drawing fatty materials and fluids therethrough. The particular open cannula tube configuration selected is dependent upon the patient and the doctor preference.

As set out above, the cannula 52 is to be easily removed and re-installed during the practice of a medical procedure by simple depression of the cannula coupling trigger 44 and pulling the cannula coupling end 50 out from the cannula coupling 42. Thereby, a number of different shapes and sizes of open cannula tubes 55 can be employed during a surgical procedure. To facilitate such use a thumb grip depression 55a, as shown in FIG. 1, is provided in the cannula handle 54. This depression 55a receives an operator's thumb and assists in guiding the open cannula tube 55 as it is urged under the patient's skin.

To facilitate sterilizing the patient contacting portions of the aspirator 10 the cannula handle 54 is preferably manufactured from a plastic material such as a Pocan KU-7600-NT supplied by Mobay Chemical of Pittsburg, Pa., that has been found to be suitable for sterilization in a conventional autoclave. The open cannula tube 55 is preferably formed from a metal that is suitable also for such autoclave sterilization such as a surgical grade 304 stainless steel. The various tubes linking the cannula through the filter 41a to bottles 34 and 38 and to the vacuum port 18 are each preferably a flexible plastic tubing, and a tubing identified as polyprophylene, has been use successfully for this application. This tubing is preferably replaced after each use.

Above has been set out the preferred configuration of the respective vessels or bottles 34 and 38 and cannula 52 for use in a liposuction surgical procedure. The respective bottles and cannula can be sterilized for re-use while the tubing is preferably intended for single use only and is then disposed of. Accordingly, it should be understood, the connector, filter and cannula coupling ends that receive the respective tubes and fitted thereover will be appropriately ridged or otherwise contoured to provide for sealing and ease of release of a tube fitted thereover. So arranged, a vacuum will be provided at the open end of the cannula tube 55 that will be effectively the vacuum that is available at the vacuum port 18.

As set out above, as the respective bottles 34 and 38 are filled, it may be necessary to change or replace one or both of them during the procedure. This is done by discontinuing the vacuum and removing the stoppers, 35 and 39 from their respective vessel or bottle 34 or 38 and lifting that bottle out of a bottle carrier or caddy 56. The bottle carrier 56, as shown best in FIGS. 1 and 2 includes, on opposite ends thereof, upstanding cups 57. Cups 57 are each molded or otherwise formed as upstanding arcuate walls in the caddy ends to accommodate the base and bottom end portion of one of the identical bottles 34 and 38. The bottle caddy 56 further includes upstanding T-shaped brackets 58 that each face towards the upstanding cups 57 walls, with, arms or wings of brackets 58 to flex so as to press against a bottle surface, urging it towards the opposite upstanding cup 57 wall, thereby holding that bottle 34 or 38 in place. As shown in FIG. 2, the bottle caddy 56 has an upstanding rear wall with a center longitudinal notch 59 formed therein. This notch 59 will receive, as shown best in FIG. 1, one leg 61 of a bracket 60 secured to extend from housing 11 top. The bracket leg 61 is fitted over the longitudinal notch 59, holding the bottle caddy to the housing 11 top. To remove or replace that bottle caddy 56, with or without bottles 34 and 38 therein, a hand access slot 62 is formed centrally in the housing top. Slot 62 is to receive an operator's hand fitted therein to contact the undersurface and edge of that bottle caddy 56 opposite to its upstanding rear wall. So arranged, the operator's fingers will be in contact with a central portion of the bottle caddy, allowing the operator to lift or rotate that caddy out of engagement with the bracket finger 61, removing it off from the housing, as illustrated in FIG. 1.

In practice, the bottle caddy 56 is preferably formed from a plastic material such that the arms of the T-shaped brackets 58 thereof will be somewhat flexible to allow the respective bottles 34 and 38 to be conveniently fitted therein. The bottle caddy 56 arrangement allows the bottles 34 and 38 to be removed as a unit with or without the stoppers installed therein, facilitating changing bottles during a liposuction surgical procedure and clean-up after the procedure.

In a practice of a liposuction surgical procedure, to change bottles 34 and 38 it is necessary to discontinue the vacuum, allowing the respective stopper 35 or 39 to be removed from over bottle open neck ends. To provide the off/on of the vacuum system, the switch 27 can be manually depressed. Alternatively, the present invention provides for remote off/on operation of the vacuum pumps through a foot switch 65, as shown in FIGS. 1 and 2. Foot switch 65 is linked by electrical cable or wire 66 to a plug 67 end. As illustrated in FIG. 2, plug end 67 is for connection into an appropriate female receptacle in housing 11. The foot switch 65, when connected, will serve as an off/on switch for the apparatus to include operating the fan, not shown.

The aspirator 10 of the present invention is intended to be portable, and accordingly, incorporates the described casters 19 that are mounted on base plate ends 13 at the corners thereof. Casters 19 allow the apparatus to be rolled smoothly along a floor. In such movement the apparatus is preferably controlled by an operator through handle 22. Handle 22, as shown in FIGS. 1, 2 and 3, incorporates lateral cross pieces 23a and 23b the are secured to opposite ends thereof, and is bent at equal distances from the cross piece end at equal angles from the horizontal. So arranged, with the handle cross piece ends 23a and 23b connected to the housing top, a knurled center portion 24 thereof will be available to receive an operator's hand fitted thereunder. Appropriately, the housing 11 top surface is contoured with depression 68 formed therein to accommodate such operator's hand fitted therein to encircle the knurled center portion 24 of the handle 22. Additional to the handle 22 positioning shown in FIG. 1, the handle 22 can be disconnected from the housing top at its one cross piece end 23a by removal of a pin 69 and rotated as shown in FIG. 3. Pin 69, shown in FIG. 2, is for fitting through holes formed in parallel housing top left side dogs or tabs 70 that extend outwardly and parallel to one another from the housing top surface. The pin 69 is to travel between aligned openings through said tabs and through the cross piece 23a, to maintain the handle to the housing top as shown in FIG. 1. When released, by withdrawal of pin 69 out from the tabs 70, the opposite handle cross piece 23b end allows pivoting, as shown in FIG. 2. The handle cross piece 23a end can then be used as a hand engaging surface for an operator to grip to drag the aspirator 10 traveling on casters 19.

To provide a pivoting capability to handle 22, at cross piece 23b, as shown in FIG. 2, bolts 71, or the like, are fitted or turned through the respective openings in the right side dogs or tabs 70 that extend outwardly and parallel to one another from the housing top.

The respective dogs or tabs 70 are constructed such that when the housing 11 is fitted to the base plate 12, as shown in FIGS. 1 and 2, the upright standards 20 ends will travel therein. So arranged, the openings 21 through the upright standards 20 will align with the openings through these tabs 70. The weight of the aspirator 10, with the handle 22 in the carrying attitude, as shown in FIGS. 1 and 3, is thereby translated through the handle cross pieces 23a and 23b to the upright standards 20 and base plate 12. So arranged, handle 22, as shown in FIG. 3, can be used to lift the apparatus by an operator fitting his hand around the handled knurled portion 24.

As set out above, the housing 11 is configured to just fit onto the plate base 12 such that the base plate upright standards 20 ends travel into the dogs or tabs 70, the holes through these dogs or tabs aligning with the holes 21 in those upright standards 20. Holes 21 therefore accommodate either the pivotal coupling of the handle cross piece 23b in the housing top right side or the releasable pin 69 coupling of the other handle cross piece 23a to the left side of the housing top. Shown best in FIG. 2, pin 69 is preferably a locking pin and for this function includes a seat formed in a rod 73 pointed end thereof that accommodates a round ball 72 seated therein. A spring biased pin 75 is fitted longitudinally within the rod 73, an end thereof extending out from the rod 73 end that is adjacent to a handle 74 end. The pin 75 exposed end, when manually depressed, will release the ball 72 seated in the rod 73, near the point end, allowing that ball 72 to recess into its seat. The pin 69 is thereby released, allowing it to be pulled from and through the dogs or tabs 70 openings, allowing the handle 22 to be rotated to the attitude shown in FIG. 3.

Hereinabove has been described the functioning of the preferred aspirator 10 of the present invention for use by a surgeon, or like qualified operator, to perform a liposuction surgical procedure to remove fat and bodily fluids from a person's body. While a preferred form or embodiment of the invention has been shown and described herein it should be understood that the invention can be embodied in other arrangements or configurations without departing from the spirit or essential character thereof. The present disclosure, it should be understood, is therefore made by way of illustration only and variations thereto are possible within the scope of this disclosure without departing from the subject matter coming within the scope of the following claims, which claims I regard as my invention.

I claim:

1. A surgical aspirator comprising, a housing having a top surface with equal opposite (leads) ends and front and rear faces and is mounted to a base plate that is supported at its corners to roll on caster means and contains means for generating, on demand, a vacuum that is available at a vacuum port that projects from said housing and is open to receive a vacuum hose means fitted thereover; cannula means that includes an open tube fitted to a handle means that is for receiving an operator's hand fitted therearound, the open tube for connection to said vacuum hose means; a pair of vacuum bottles with stoppers that include hose connectors for serial connection in said vacuum hose means; bottle caddy means for maintaining said pair of vacuum bottles arranged for releasable mounting to said housing top surface that is molded to include a recess to maintain the bottle caddy means nested therein, and the releasable mounting is a U-shaped bracket that includes parallel legs that extend outwardly from ends of a web portion thereof, the one U-shaped bracket leg for connection to the housing top surface at the center of the interior edge of the bottle caddy means recess, the U-shaped bracket other leg to extend over and to contact an edge of said bottle caddy means when said bottle caddy means is seated or nested on said housing.

2. A surgical aspirator as recited in claim 1, further including a recess centrally molded into the housing, below said bottle caddy recess and having dimensions for receiving an operator's hand fitted therein to grasp said bottle caddy means edge.

3. A surgical aspirator as recited in claim 1, wherein the vacuum port and a vacuum control valve handle extend upwardly from the housing top surface; and a said vacuum control valve handle is connected to the means for generating, on demand, a vacuum and is arranged to be manually operated to control the vacuum available at said vacuum port.

4. A surgical aspirator as recited in claim 3, further including gauge means arranged in the switch and gauge panel of the housing top surface to visually display the vacuum availability at the vacuum port; and manual off/on switch means arranged on said switch and gauge panel for controlling operation of the means for generating, on demand, a vacuum.

5. A surgical aspirator as recited in claim 4, further including foot switch means and means for connecting said foot switch means to override the manual switch means on depressing a foot engaging portion thereof.

6. A surgical aspirator as recited in claim 1, wherein the means for generating a vacuum, on demand, is an electric motor turning dual rotary vane oilless pumps.

7. A surgical aspirator as recited in claim 6, wherein the electric motor is a one third (⅓) horse power motor and the dual vane oilless pumps are mounted to the opposite ends of said electric motor.

8. A surgical aspirator as recited in claim 1, further including a filter means that is serially arranged in the vacuum hose means between the vacuum port and the hose connector of a bottle stopper for prohibiting passage of fluid materials to said vacuum port.

9. A surgical aspirator as recited in claim 1, wherein the cannula means is a tube that is open longitudinally and includes the handle means secured to one end thereof, with said handle means contoured to accommodate an operator's hand fitted therearound, the handle means further including a quick release coupling means for joining said cannula handle means end to an end of the vacuum hose means, said quick release coupling means to allow said handle means to rotate freely through three hundred sixty (360) degrees around said vacuum hose means end.

10. A surgical aspirator as recited in claim 9, wherein the cannula handle means includes a thumb depression in a top surface thereof, and is formed of a material to be suitable to be sterilized by heating as in an autoclave sterilization unit.

11. A surgical aspirator comprising, a housing having a top surface with equal opposite ends and front and rear faces that is arranged to fit on a rectangular base plate that is supported at its corners to roll on a caster means with pairs of upright standards secured to extend parallel at a normal angle from opposite ends of said base plate, the individual upright standards spaced apart from a longitudinal center axis of said base plate and are identically holed proximate to their unconnected ends, said holes of each pair to align with holes formed in pairs of outwardly extending tab means that are formed in said housing top surface, said tab means to receive the holed ends of said upright standards fitted therein, the holes therethrough to align; handle means that includes lateral cross pieces on opposite ends thereof that are open therethrough and are of a length to fit between said tab means; fastener means to fit through said handle means lateral cross pieces and tab means and upright standard holes, for securing said handle means lateral cross pieces between said tab means; means for generating, on demand, a vacuum available at a vacuum port that projects from said housing and is open to receive a vacuum hose means fitted thereover; cannula means that includes an open tube fitted to a handle means that is for receiving an operator's hand fitted therearound, the open tube for connection to said vacuum hose means; at least one vacuum bottle means with stopper with a hose connector for connection to said vacuum hose means; and bottle caddy means for maintaining said vacuum bottle to said housing.

12. A surgical aspirator as recited in claim 11, wherein the fastener means is a pair of bolts, each bolt of the pair turned through an opposite aligned tab means hole, fitting through the upright standard hole, and into one end of the handle means lateral cross piece fitted therebetween; and pin means for releasable fitting through the aligned holes in said other pairs of tab means and upright standards into through the other handle means lateral cross piece end.

13. A surgical aspirator as recited in claim 11, wherein the handle means is bent at distances equidistant from the handle means lateral cross piece ends at equal angles below the horizontal; and a handle means mid-portion is knurled.

14. A surgical aspirator as recited in claim 1, further including a recess formed in the housing top surface immediately below of the handle means knurled mid-portion when said handle means is secured at its lateral cross piece ends between the housing tab means.

15. A surgical aspirator comprising, a housing having a top surface with equal opposite ends and front and rear faces that is arranged to roll on caster means and contains means for generating, on demand, a vacuum that is available at a vacuum port that projects from said housing and is open to receive a vacuum hose means fitted thereover; cannula means that includes an open tube fitted to a handle means that is for receiving an operator's hand fitted therearound, the open tube for connection to said vacuum hose means; a pair of vacuum bottles with stoppers that include hose connectors for serial connection in said vacuum hose means; bottle caddy means for maintaining said pair of vacuum bottles arranged for releasable mounting to said housing consisting of an essentially flat plate web member that is arranged between open bottle receptacle means formed on opposite ends thereof that are each for maintaining the bases of vacuum bottles thereon, said bottle receptacle means each including an arcuate upstanding wall that extends at a normal angle from an outside end of a flat circular surface, with an upstanding bracket having arms forming, essentially, a T-shaped extending at a normal angle from the opposite edge of each said flat circular surface, each said bracket arm bent towards the arcuate wall opposite thereto to flex against a vacuum bottle positioned therebetween.

16. A surgical aspirator as recited in claim 15, wherein the T-shaped brackets of the bottle receptacle means are formed of a flexible material to flex away from the side of a vacuum bottle seated in the bottle receptacle means.

17. A surgical aspirator as recited in claim 15, further including an upstanding wall formed at a normal angle from an inside edge of the essentially flat plate web member between the arcuate upstanding walls of the bottle receptacle means, which upstanding wall is centrally notched to receive a releasable mounting means of the aspirator housing fitted thereover.

18. A surgical aspirator as recited in claim 15, wherein the bottle caddy means is formed as a single unit from a plastic material.

* * * * *